United States Patent [19]

Vogel et al.

[11] 4,298,535

[45] Nov. 3, 1981

[54] ANTHRACYCLINONES

[75] Inventors: Pierre Vogel; Pierre-Alain Carrupt, both of Lausanne, Switzerland

[73] Assignee: Hoffmann-La Roche Inc., Nutley, N.J.

[21] Appl. No.: 198,498

[22] Filed: Oct. 20, 1980

Related U.S. Application Data

[62] Division of Ser. No. 139,532, Apr. 11, 1980, Pat. No. 4,264,510.

[30] Foreign Application Priority Data

Apr. 20, 1979 [CH] Switzerland .......................... 3751/79
Jan. 31, 1980 [CH] Switzerland ............................ 783/80

[51] Int. Cl.³ .................... C07C 50/16; C07C 69/76; C07C 50/22; C07C 69/74
[52] U.S. Cl. .................................... 260/365; 560/255; 560/256; 560/51; 560/53; 568/326; 560/56
[58] Field of Search .................... 560/255, 256, 51, 53; 568/326; 260/365, 351.1

[56] References Cited

U.S. PATENT DOCUMENTS

| | | | |
|---|---|---|---|
| 2,987,545 | 6/1961 | Kende et al. | 560/51 |
| 3,947,517 | 3/1976 | Maxfeldt et al. | 568/326 |
| 4,161,480 | 7/1979 | Pappo et al. | 260/365 |
| 4,190,602 | 2/1980 | Brunisholz et al. | 560/255 |

*Primary Examiner*—Winston A. Douglas
*Assistant Examiner*—Raymond K. Covington
*Attorney, Agent, or Firm*—Jon S. Saxe; Bernard S. Leon; Frank P. Hoffman

[57] ABSTRACT

There is presented a synthetic process for the production of anthracyclinones, the aglycones of the anthracyclines. Also disclosed are novel intermediates in the above process. The end product aglycones may thereafter be utilized to produce biologically useful products such as carminomycin or adriamycin.

7 Claims, No Drawings

ANTHRACYCLINONES

This is a division of application Ser. No. 139,532, filed Apr. 11, 1980, now U.S. Pat. No. 4,264,510.

DESCRIPTION OF THE INVENTION

The present invention is concerned with a novel synthetic approach to anthracyclinones, the aglycones of the anthracyclines, especially with the use of the known 2,3,5,6-tetramethylene-7-oxabicyclo[2.2.1]heptane (I, Tetrahedron Lett. 1976, 4271) for their manufacture and novel polycyclic compounds which are obtained as intermediates.

The process provided by the invention comprises reacting 2,3,5,6-tetramethylene-7-oxabicyclo[2.2.1.]-heptane (I) with a suitable dienophile to give 1,2,3,4,8a,10,10a-octahydro-2,3-dimethylene-1,4-epoxyanthracene-5,8-dione (II), 1,2,3,4,9,10-hexahydro-2,3-dimethylene-1,4-epoxyanthracene (III) or a compound of the general formula

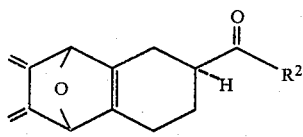

wherein $R^2$ represents a methyl or lower alkoxy group, if desired, isomerising the compound II in the presence of catalytic amounts of an acid or base to give 1,2,3,4,9,10-hexahydro-5,8-dihydroxy-2,3-dimethylene-1,4-epoxyanthracene (V) and methylating this compound V to give 1,2,3,4,9,10-hexahydro-5,8-dimethoxy-2,3-dimethylene-1,4,-epoxyanthracene (VI), or reducing the compound II to give a compound of the formula

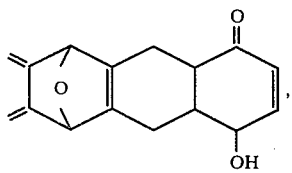

converting this compound XX into a compound of the formula

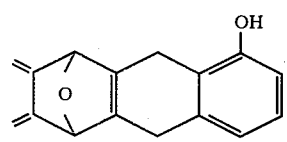

and, if desired, etherifying this compound XXI to give a compound of the general formula

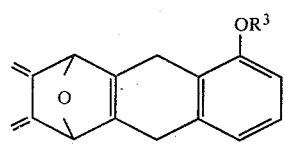

wherein $R^3$ represents a methyl or benzyl group, if desired, reacting a compound of the general formula

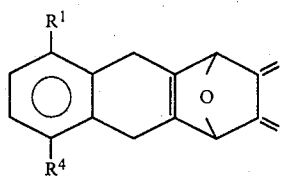

wherein $R^1$ represents a hydrogen atom or a hydroxy or methoxy group and $R^4$ represents a hydrogen atom or a hydroxy, methoxy or benzyloxy group,
with a suitable dienophile in a diene synthesis to give a compound of the general formula

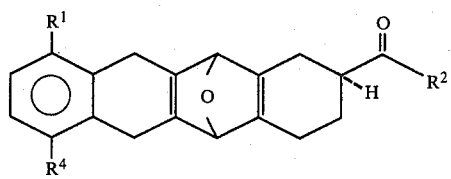

wherein $R^1$, $R^2$ and $R^4$ have the significance given earlier,
if desired, reacting a resulting compound of the formula IV with 1,4-benzoquinone or dehydrobenzene in a diene synthesis to give a compound of the general formula

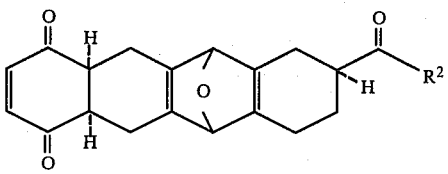

or

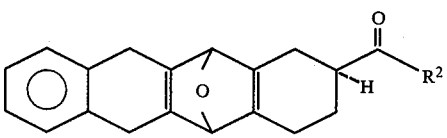

wherein $R^2$ has the significance given earlier,
if desired, isomerising a compound IX in the presence of catalytic amounts of an acid or base to give a compound of the general formula

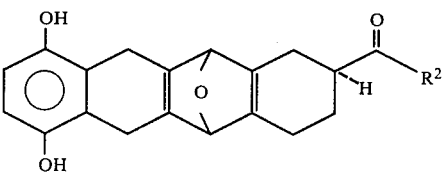

wherein $R^2$ has the significance given earlier,
and methylating this compound XI to give the corresponding dimethoxy compound of the general formula

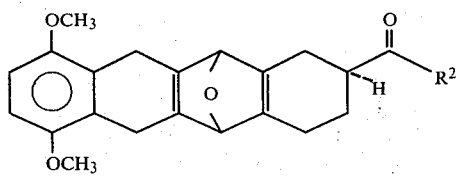

wherein R² has the significance given earlier,
if desired, dehydrogenating a compound of formula VII or VIII to give a compound of the general formula

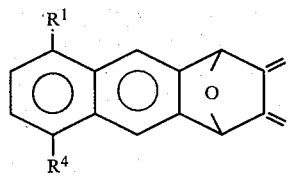

or

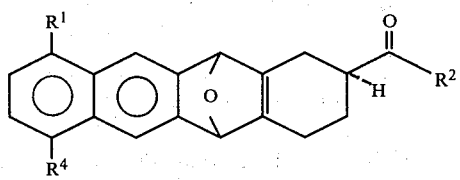

wherein R¹, R² and R⁴ have the significance given earlier,
or, if desired, reacting a compound of formula XIII with a suitable dienophile in a diene synthesis to give a compound of the formula XIV, if desired, opening the epoxide ring present in a compound of formula XIV and acetylating the resulting mixture of the corresponding 5- and 12-hydroxy compounds, if desired after prior oxidation to a compound of the general formula

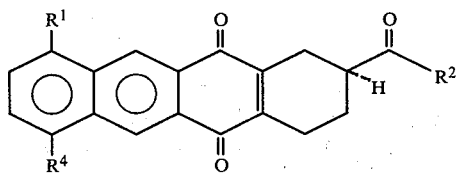

wherein R¹, R² and R⁴ have the significance given earlier,
to give a compound of the general formula

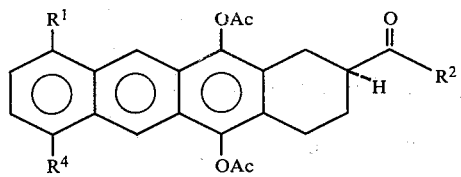

wherein R¹, R² and R⁴ have the significance given earlier and Ac represents an acetyl group,
and, if desired, oxidising this compound of formula XVI to give a quinone of the general formula

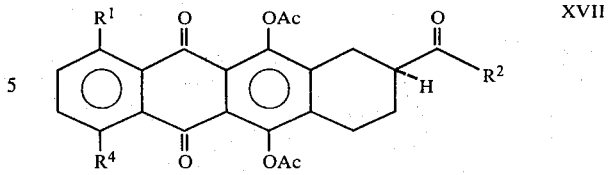

wherein $R^1$, $R^2$, $R_4$ and Ac have the significance given earlier.

The key reaction of the synthesis provided by the present invention is the reaction of the compound I with a suitable dienophile to give a compound II, III or IV. Suitable dienophiles are 1,4-benzoquinone, dehydrobenzene, methyl vinyl ketone and derivatives thereof such as H₃C—COO—C(=CH₂)—CO—CH₃, C₆H₅—COO—C(=CH₂)—CO—CH₃ or (H₃C)₃Si-O—C(=CH₂)—CO—CH₃, or acrylic acid lower alkyl esters, the methyl ester being preferred.

The reaction is carried out in a manner known per se under the conditions of a Diels-Alder addition using equimolar amounts of the diene and of the dienophile. The reaction gives high yields of the sterically correct product. The dehydrobenzene is generated in situ in a known manner (e.g. from anthranilic acid).

The isomerisation of the resulting 1,2,3,4,8a,9,10,10a-octahydro-2,3-dimethylene-1,4-epoxyanthracene-5,8-dione (II) to give the corresponding 5,8-dihydroxy compound V and the etherification of the latter to give 1,2,3,4,9,10-hexahydro-5,8-dimethoxy-2,3-dimethylene-1,4-epoxyanthracene (VI) can be carried out in a manner known per se by treatment with a small amount of an acid or base (e.g. silicic acid) and subsequent methylation (e.g. with methyl iodide).

Both reactions can be carried out with almost quantitative yield also in one step by treating the compound II with for example, methyl iodide in the presence of potassium carbonate.

The reduction of the 5,8-dione of formula II to give the 8-hydroxyanthracen-5-one of formula XX can be carried out in a manner known per se by treatment with an equivalent amount of a complex hydride (e.g. diisobutyl aluminium hydride, lithium aluminium hydride or tetra-n-butylammonium borohydride) in an inert organic solvent. The reduction can also be carried out with sodium borohydride and ammonium chloride, although in this case somewhat lower yields of the desired product are obtained.

The dehydration of the 8-hydroxyanthracen-5-one of formula XX to give the anthracen-5-ol of formula XXI is conveniently effected by mesylation or tosylation and subsequent cleavage of methanesulphonic acid or toluenesulphonic acid in a manner known per se using a base, with simultaneous aromatisation of the A-ring. Finally, by methylation or benzylation in the usual manner there is obtained the corresponding methyl or benzyl ether of formula XXII.

Now, in optional sequence, a compound of formula VII obtained can be aromatised in ring B and subjected to a further Diels-Alder addition. The dehydrogenation can be carried out, for example, using an appropriately substituted quinone such as 2,3-dichloro-5,6-dicyano-1,4-benzoquinone or chloranil in an inert solvent. Suitable dienophiles which can be used for the further synthesis of the polycyclic system include acrylic acid esters, preferably methyl acrylate, or methyl vinyl ketone or the previously mentioned derivatives thereof.

There is thus obtained from a compound VII either firstly a compound XIII which is then converted into a compound XIV by Diels-Alder addition, or a compound VIII which can then be dehydrogenated to give compound XIV.

On the other hand, a compound of the formula IV can be converted into a compound IX or X by Diels-Alder addition of 1,4-benzoquinone or dehydrobenzene in a manner known per se and analogously to the aforementioned conversion of compound I into compound II or compound III.

The compound IX can be isomerised to give a compound XI which can then be methylated to give compound XII in analogy to the conversion of compound II into compound V and conversion of the latter into compound VI.

A 5,12-epoxy compound XIV can be converted, with opening of the epoxide ring, into a mixture of the corresponding 5- and 12-hydroxy compounds by treatment with an acid (e.g. trifluoroacetic acid) in an inert organic solvent (e.g. chloroform or benzene). If this treatment is carried out in the presence of acetic anhydride, then there is obtained a mixture of corresponding 5- and 12-acetoxy compounds. The mixture can be separated by chromatography, although this is not essential for the further course of the synthesis because by using Tl(OAc)$_3$.1½H$_2$O as the acetylating agent at room temperature in the presence of acetic anhydride there is obtained from the mixture of the 5- and 12-hydroxy compounds the 5,12-diacetoxy compound XVI. On the other hand, the mixture of the 5- and 12-hydroxy compounds can be oxidised, for example, with PbO$_2$ or atmospheric oxygen in an acid medium, preferably acetic acid, at room temperature, to give the quinone of formula XV which can then be reductively acetylated to give the 5,12-diacetoxy compound XVI. This can be carried out, for example, by heating to reflux for a short time with zinc dust in acetic anhydride.

Finally, a compound XVI can be converted into a compound XVII in a manner known per se by oxidation with an oxidation agent such as chromic acid in acetic acid at room temperature.

The compounds of formulae II–XVI and XX–XXII are novel compounds and also form part of the present invention, while compounds of formula XVII are already known and can be converted in a known manner into biologically active anthracyclines; for example, via the following intermediates:

The novel aglycones of the present invention can be converted into pharmaceutically useful end products by following methods well-known in the art, for example, the following steps:

(a) Introduction of hydroxy group in position 9: Cava et al., J. Am. Chem. Soc. 100, 3635 (1978), (b) Introduction of hydroxy group in position 7: Wong et al., Can. J. Chem. 49, 2712 (1971), (c) Glycosylation: Annual reports in Medicinal Chemistry, Vol. 14, Editor H. J. Hess, Academic Press, New York, San Francisco, London, 1979, p. 288 (Synthetic Approaches to Anthracycline Antibiotics).

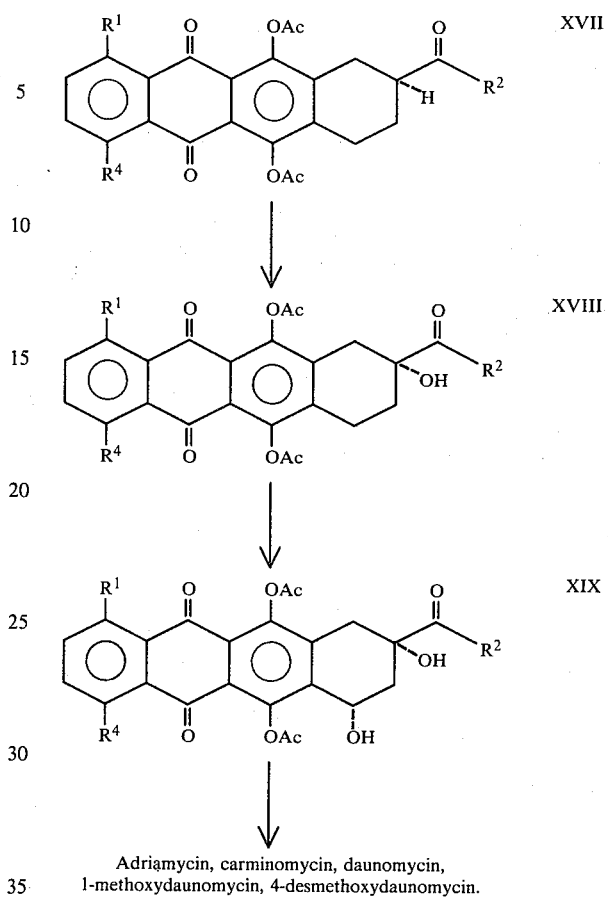

Adriamycin, carminomycin, daunomycin, 1-methoxydaunomycin, 4-desmethoxydaunomycin.

The following Examples illustrate the present invention.

EXAMPLE 1

A mixture of 2 g (13.7 mmol) of 2,3,5,6-tetramethylene-7-oxabicyclo[2.2.1]heptane, 1.47 g (13.7 mmol) of freshly sublimed p-benzoquinone and 20 ml of chloroform was heated at 80° C. for 5 hours under nitrogen. After cooling, the mixture was concentrated to dryness and recrystallised from acetone/methanol (4:1). There were obtained 3.28 g (95%) of 1,2,3,4,8a,9,10,10a-octahydro-2,3-dimethylene-1,4-epoxyanthracene-5,8-dione of melting point 147° C. (decomposition) in the form of yellow crystals.

11.21 g (79 mmol) of methyl iodide were added dropwise under nitrogen to a mixture of 2 g (7.9 mmol) of 1,2,3,4,8a,9,10,10a-octahydro-2,3-dimethylene-1,4-epoxy-anthracene-5,8-dione, 10.9 g (79 mmol) of dried potassium carbonate and 100 ml of anhydrous acetone. The mixture was heated at 80° C. for 15 hours, filtered, the filtrate was concentrated, the residue was taken up in 80 ml of chloroform and the solution was washed with three 40 ml portions of water. After drying over magnesium sulphate, concentration and recrystallisation from diethyl ether/tetrahydrofuran/methylene chloride (4:1:2), there were obtained 2.05 g (92%) of 1,2,3,4,9,10-hexahydro-5,8-dimethoxy-2,3-dimethylene-1,4-epoxyanthracene of melting point 177°–178° C. in the form of white crystals.

A mixture of 2 g (7.1 mmol) of 1,2,3,4,9,10-hexahydro-5,8-dimethoxy-2,3-dimethylene-1,4-epoxyanthracene, 1.77 g (7.8 mmol) of 2,3-dichloro-5,6-dicyano-1,4- benzoquinone and 30 ml of benzene was stirred at room temperature under nitrogen for 30 minutes. The precipitate formed was filtered off and washed with benzene, the benzene solution was washed with two 30 ml portions of saturated aqueous sodium hydrogen sulphite solution and two 30 ml portions of water, dried over sodium sulphate and concentrated to dryness. By recrystallisation from diethyl ether/tetrahydrofuran/methylene chloride (4:1:2) there were obtained 1.95 g (98%) of 1,2,3,4-tetrahydro-5,8-dimethoxy-2,3-dimethylene-1,4-epoxyanthracene of melting point 205°-206° C. in the form of white crystals.

A mixture of 3 g (10.7 mmol) of 1,2,3,4-tetrahydro-5,8-dimethoxy-2,3-dimethylene-1,4-epoxyanthracene and 30 ml of methyl vinyl ketone was heated at 90° C. for 24 hours under nitrogen. Excess methyl vinyl ketone and oligomer formed by the heating were removed by distillation at 110° C. under reduced pressure ($10^{-2}$ mmHg). The residue was recrystallised from tetrahydrofuran/methylene chloride/hexane (3:3:5) and yielded 3.5 g (93%) of (1,2,3,4,5,12-hexahydro-7,10-dimethoxy-5,12-epoxynaphthacen-2-yl) methyl ketone of melting point 167°-168° C. in the form of a white amorphous powder.

0.2 ml of trifluoroacetic acid was added under nitrogen to a solution of 1 g (2.9 mmol) of (1,2,3,4,5,12-hexahydro-7,10-dimethoxy-5,12-epoxynaphthacen-2-yl) methyl ketone in 10 ml of chloroform. The mixture was stirred at room temperature for 30 minutes, diluted with 30 ml of chloroform and extracted with three 20 ml portions of saturated sodium bicarbonate solution. The extract was dried over magnesium sulphate and concentrated to dryness. The resulting mixture of (1,2,3,4,5,12-hexahydro-5- and -12-hydroxy-7,10-dimethoxy-2-naphthacenyl) methyl ketone was dissolved in acetic anhydride and treated at room temperature for 1 hour with 5 mol equivalents of thallium (III) acetate. After the addition of 5 mol equivalents of pyridine, the mixture was again stirred at room temperature for 1 hour, diluted with water and extracted with chloroform. The chloroform extract was washed with 2 N hydrochloric acid and saturated sodium bicarbonate solution and concentrated to dryness. Chromatography on silica gel gave 2-acetyl-1,2,3,4-tetrahydro-7,10-dimethoxy-5,12-naphthacenylene-diacetate of melting poing 232°-233° C. (from hexane) in 45% yield.

A solution of 90 mg (0.9 mmol) of chromic acid in 2 ml of acetic acid was added to a solution of 100 mg (0.22 mmol) of 2-acetyl-1,2,3,4-tetrahydro-7,10-dimethoxy-5,12-naphthacenylene-diacetate in 2 ml of acetic acid. The mixture was stirred at room temperature for 2 hours, diluted with chloroform and water, washed with saturated sodium hydrogen carbonate solution, dried over magnesium sulphate and concentrated to dryness. Recrystallisation from ethyl acetate/hexane (2:1) yielded 2-acetyl-1,2,3,4,6,11-hexahydro-7,10-dimethoxy-6,11-dioxo-5,12-naphthacenylene-diacetate.

EXAMPLE 2

In a manner analogous to that described in Example 1, a mixture of 1,2,3,4-tetrahydro-5,8-dimethoxy-2,3-dimethylene-1,4-epoxyanthracene and methyl acrylate was reacted to give 1,2,3,4,5,12-hexahydro-7,10-dimethoxy-5,12-epoxynaphthacene-2-carboxylic acid methyl ester which was converted via 5,12-diacetoxy-1,2,3,4-tetrahydro-7,10-dimethoxy-2-naphthacenecarboxylic acid methyl ester into 5,12-diacetoxy-1,2,3,4,6,11-hexahydro-7,10-dimethoxy-6,11-dioxo-2-naphthacenecarboxylic acid methyl ester.

EXAMPLE 3

A mixture of 11.4 g of 2,3,5,6-tetramethylene-7-oxabicyclo[2.2.1]heptane, 2 g of anhydrous zinc chloride, 30 ml of methyl vinyl ketone and 75 ml of chloroform, containing 10 mg of hydroquinone, was stirred at room temperature for 20 hours under nitrogen. The mixture was concentrated under reduced pressure (ca 15 mmHg, room temperature) and rapidly eluted with methylene chloride/ethyl acetate (2:1) on a short column filled with 18 g of $SiO_2$ (70-230 mesh). The first fractions contained methyl (1,2,3,4,5,6,7,8-octahydro-2,3-dimethylene-1,4-epoxynaphthalen-6-yl) ketone and unreacted methyl vinyl ketone. After the addition of 5 mg of hydroquinone, the mixture was concentrated to dryness at room temperature under reduced pressure (1 mmHg) until the methyl vinyl ketone had been completely removed. There were obtained 14.5 g (86%) of methyl (1,2,3,4,5,6,7,8-octahydro-2,3-dimethylene-1,4-epoxynaphthalen-6-yl) ketone in sufficient purity for the next step.

By distillation under reduced pressure there was obtained in 71% yield pure methyl (1,2,3,4,5,6,7,8-octahydro-2,3-dimethylene-1,4-epoxynaphthalen-6-yl) ketone in the form of a colourless oil (b.p. $_{0.1}$ 120° C.) consisting of a mixture of diastereomers (95:5).

To a solution of 11.4 g of methyl (1,2,3,4,5,6,7,8-octahydro-2,3-dimethylene-1,4-epoxynaphthalen-6-yl) ketone in 60 ml of 1,2-dimethoxyethane were added portionwise at 85° C. during 60 minutes 14.5 g of anthranilic acid in 90 ml of 1,2-dimethoxyethane simultaneously with 12.3 g of pentyl nitrite in 90 ml of 1,2-dimethoxyethane. The mixture was heated at 85° C. until gas evolution has ceased (20-45 minutes) and, after cooling to room temperature, treated with 100 ml of 10% aqueous potassium hydroxide and 200 ml of ether. The aqueous phase was extracted four times with 100 ml of ether each time, the ether extract was washed four times with 100 ml of water each time, dried over sodium sulphate and concentrated. 15 ml of dipropyl ether/methanol (3:1, v/v) were added to the residue. The precipitate was filtered off and washed with 10 ml of the foregoing dipropyl ether/methanol mixture. 5.4 g (35%) of a mixture of 85% methyl (1,2,3,4,5,6,11,12-octahydro-5,12-epoxynaphthacen-2-yl) ketone and 15% (1,2,3,4,5,12-hexahydro-5,12-epoxynaphthacen-2-yl) methyl ketone were obtained. The yield could be increased to 50% by chromatography of the mother liquor on aluminium oxide (neutral).

A solution of 0.65 g of 2,3-dichloro-5,6-dicyano-1,4-benzoquinone in 30 ml of benzene was added to a solution of 0.8 g of the obtained according to the previous paragraph in 20 ml of benzene. After 3 hours at room temperature, the precipitate was filtered off and washed with benzene. The benzene phase was washed with 50 ml of saturated aqueous sodium hydrogen sulphite solution and water until it had been completely decolourised, dried over sodium sulphate and concentrated to dryness. There were obtained 754 mg (95%) of (1,2,3,4,5,12-hexahydro-5,12-epoxynaphthacen-2-yl) methyl ketone of melting point 158°-160° C. (from ethanol).

A mixture of 0.68 g of (1,2,3,4,5,12-hexahydro-5,12-epoxynaphthacen-2-yl) methyl ketone, 15 ml of chloroform and 0.9 ml of trifluoroacetic acid was left to stand at room temperature for 20 hours, neutralised with sodium hydrogen carbonate and extracted with methylene chloride. The extract was dried over sodium sulphate and concentrated to dryness. The residue was treated with 50 ml of methylene chloride, 1 ml of diethyl ether and 12 g of silicic acid and the mixture was stirred in the air for 48 hours. After concentration to dryness, the residue was chromatographed on silicic acid. There were obtained 475 g (38%) of crude 2-acetyl-1,2,3,4-tetrahydro-5,12-naphthacenedione which, after washing with methanol, had a melting point of 189°–192° C. (from ethanol).

A mixture of 178 mg of 2-acetyl-1,2,3,4-tetrahydro-5,12-naphthacenedione, 700 mg of zinc dust and 10 ml of acetic anhydride was heated at 115° C. for 40 minutes under nitrogen. The solid residue was filtered off and washed with three 10 ml portions of chloroform. Excess acetic anhydride was removed by the addition of aqueous sodium hydrogen carbonate (3 hours stirring at 20° C.). The mixture was extracted with three 10 ml portions of chloroform, the chloroform extract was dried over sodium sulphate and concentrated to dryness. There were obtained 223 mg (98%) of crude 2-acetyl-1,2,3,4-tetrahydro-5,12-naphthacenylene-diacetate.

After washing with 3 ml of ether, there were obtained 175 mg (77%) of colourless crystals of melting point 226°–229° C. (from chloroform/ethanol).

A mixture of 221 mg of 2-acetyl-1,2,3,4-tetrahydro-5,12-naphthacenylene-diacetate and 0.2 g of chromic acid in 10 ml of 80% aqueous acetic acid was stirred at 20° C. under nitrogen for 2 hours. After the addition of 20 ml of chloroform and neutralisation with aqueous sodium hydrogen carbonate, the mixture was extracted with three 10 ml portions of chloroform, the extract was dried over sodium sulphate and concentrated to dryness. The crude product (225 mg) was recrystallised from methanol and yielded 131 mg (55%) of 2-acetyl-1,2,3,4,6,11-hexahydro-6,11-dioxo-5,12-naphthacenylene-diacetate of melting point 195°–198° C.

EXAMPLE 4

A solution of 3.38 g of 1,2,3,4,8a,9,10,10a-octahydro-2,3-dimethylene-1,4-epoxyanthracene-5,8dione in 50 ml of methylene chloride and 50 ml of methanol was cooled to −70° C. and treated under nitrogen with 2.04 g of tetra-n-butylammonium borohydride in 10 ml of methylene chloride. The mixture was then stirred at −70° C. for 1.75 hours. After the addition of 100 ml of aqueous ammonium chloride solution, the solution was stirred for a further 1 hour. The phases were separated, the aqueous phase was extracted twice with 50 ml of methylene chloride each time and the combined organic phases were washed with two 100 ml portions of water and subsequently dried over magnesium sulphate. After concentration and recrystallisation, there were obtained 2.52 g (74%) of 1,2,3,4,5,8,8a,9,10,10a-decahydro-2,3-dimethylene-1,4-epoxy-8-hydroxy-anthracen-5-one of melting point 206°–207° C.

1.23 g of mesyl chloride were added to a solution, cooled to 0° C., of 2.03 g of 1,2,3,4,5,8,8a,9,10,10a-decahydro-2,3-dimethylene-1,4-epoxy-8-hydroxyanthracen-5-one in 20 ml of pyridine. The mixture was stirred at room temperature for 1.5 hours, poured into 200 ml of ice/water and yielded, after filtration and drying, 2.37 g (90%) of 1,2,3,4,5,8,8a,9,10,10a-decahydro-2,3-dimethylene-1,4-epoxy-8-mesyloxyanthracen-5-one of melting point 110° C. (with explosion).

876 mg of potassium tert.butylate were added under a nitrogen atmosphere to a solution of 2.37 g of 1,2,3,4,5,8,8a,9,10,10a-decahydro-2,3-dimethylene-1,4-epoxy-8-mesyloxyanthracen-5-one in 40 ml of tetrahydrofuran, there being formed 1,2,3,4,9,10-hexahydro-2,3-dimethylene-1,4-epoxyanthracen-5-ol. After stirring at room temperature for 1 hour, a further 877 mg of potassium tert.butylate were added. The mixture was stirred for a further 45 minutes, 1.32 ml of methyl iodide were added and the resulting mixture was stirred for a further 1 hour. The mixture was treated with 100 ml of aqueous ammonium chloride and extracted three times with 100 ml of diethyl ether each time. After washing with three 100 ml portions of ammonium chloride solution, the combined organic phases were dried over magnesium sulphate. There were obtained 1.56 g (87%) of crude 1,2,3,4,9,10-hexahydro-2,3-dimethylene-1,4-epoxy-5-methoxyanthracene of melting point 145°–147° C. (from methanol).

By reacting the 1,2,3,4,9,10-hexahydro-2,3-dimethylene-1,4-epoxyanthracen-5-ol with benzyl bromide in place of methyl iodide in an analogous manner, there was obtained in good yield 1,2,3,4,9,10-hexahydro-5-benzyloxy-2,3-dimethylene-1,4-epoxyanthracene.

1.24 g of 2,3-dichloro-5,6-dicyano-1,4-benzoquinone were added at room temperature under a nitrogen atmosphere to a solution of 1.56 g of crude 1,2,3,4,9,10-hexahydro-2,3-dimethylene-1,4-epoxy-5-methoxyanthracene in 50 ml of benzene. After 1 hour, the suspension was filtered and the filtrate was washed with benzene. The organic solution was washed with two 75 ml portions of sodium hydrogen sulphite solution and two 75 ml portions of water. The aqueous phase was extracted with 50 ml of benzene and the combined organic solutions were dried over magnesium sulphate. After concentration, the residue was dissolved in 150 ml of diethyl ether, the solution was stirred with active carbon, the mixture was filtered and subsequently the filtrate was concentrated. Crystallisation of the residue from methanol yielded 1.09 g (70%) of 1,2,3,4-tetrahydro-2,3-dimethylene-1,4-epoxy-5-methoxyanthracene of melting point 154°–155° C.

What is claimed:

1. A compound of the formula

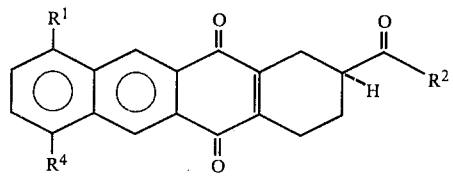

wherein $R^1$ represents a hydrogen atom or a hydroxy or methoxy group, $R^2$ represents a methyl or lower alkoxy group and $R^4$ represents a hydrogen atom or a hydroxy, methoxy or benzyloxy group with the proviso that $R^1$ and $R^4$ do not simultaneously represent a hydrogen atom.

2. A compound of the formula

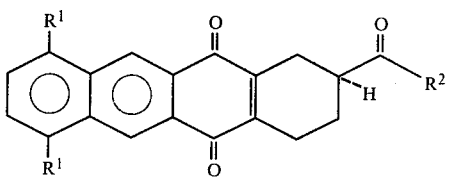

wherein R¹ represents a hydrogen atom or a hydroxy or methoxy group and R² represents a methyl or lower alkoxy group.

3. A compound of the formula

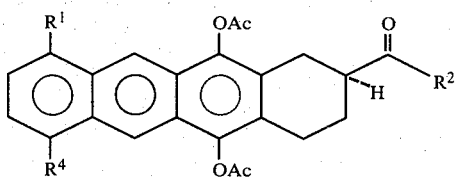

wherein Ac represents an acetyl group, R¹ represents a hydrogen atom or a hydroxy or methoxy group, R² represents a methyl or lower alkoxy group and R⁴ represents a hydrogen atom or a hydroxy, methoxy or benzyloxy group.

4. A compound of the formula

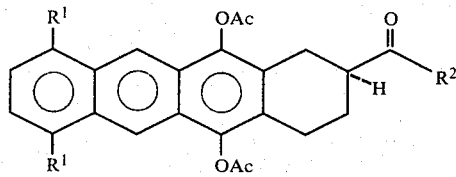

wherein Ac represents an acetyl group, R¹ represents a hydrogen atom or a hydroxy or methoxy group and R² represents a methyl or lower alkoxy group.

5. The compound: 2-Acetyl-1,2,3,4-tetrahydro-7,10-dimethoxy-5,12-naphthacenylene-diacetate.

6. The compound: 5,12-Diacetoxy-1,2,3,4-tetrahydro-7,10-dimethoxy-2-naphthacenecarboxylic acid methyl ester.

7. The compound: 2-Acetyl-1,2,3,4-tetrahydro-5,12-naphthacenylene-diacetate.

* * * * *